(12) United States Patent
Nisius

(10) Patent No.: US 7,813,478 B2
(45) Date of Patent: Oct. 12, 2010

(54) METHOD AND APPARATUS TO FACILITATE PROVISION AND USE OF MULTIPLE X-RAY SOURCES

(75) Inventor: David Nisius, Des Plaines, IL (US)

(73) Assignee: Varian Medical Systems, Inc., Palo Alto, CA (US)

( * ) Notice: Subject to any disclaimer, the term of this patent is extended or adjusted under 35 U.S.C. 154(b) by 22 days.

(21) Appl. No.: 11/672,797

(22) Filed: Feb. 8, 2007

(65) Prior Publication Data

US 2008/0192890 A1    Aug. 14, 2008

(51) Int. Cl.
*H05G 1/58* (2006.01)
*H05G 1/30* (2006.01)

(52) U.S. Cl. .......................... 378/115; 378/57; 378/92; 378/98.9; 378/196; 378/197

(58) Field of Classification Search ............ 378/9, 378/53, 57, 92, 98.9, 16, 98.11, 115, 196, 378/197
See application file for complete search history.

(56) References Cited

U.S. PATENT DOCUMENTS

| | | | |
|---|---|---|---|
| 5,182,764 A * | 1/1993 | Peschmann et al. | 378/57 |
| 5,490,196 A * | 2/1996 | Rudich et al. | 378/101 |
| 5,966,422 A | 10/1999 | Dafni et al. | |
| 6,018,562 A * | 1/2000 | Willson | 378/9 |
| 6,026,143 A * | 2/2000 | Simanovsky et al. | 378/57 |
| 6,370,223 B1 * | 4/2002 | Gleason et al. | 378/58 |
| 6,459,761 B1 * | 10/2002 | Grodzins et al. | 378/57 |
| 6,597,759 B2 * | 7/2003 | Mazess et al. | 378/53 |
| 6,813,333 B2 * | 11/2004 | Karau et al. | 378/4 |
| 6,876,719 B2 * | 4/2005 | Ozaki | 378/7 |
| 6,891,918 B2 * | 5/2005 | Drummond et al. | 378/5 |
| 6,898,263 B2 * | 5/2005 | Avinash et al. | 378/4 |
| 6,922,462 B2 * | 7/2005 | Acharya et al. | 378/98.11 |
| 7,060,981 B2 * | 6/2006 | Retterath et al. | 250/359.1 |
| 7,103,137 B2 * | 9/2006 | Seppi et al. | 378/9 |
| 7,616,731 B2 * | 11/2009 | Pack et al. | 378/10 |
| 7,684,538 B2 * | 3/2010 | Morton et al. | 378/10 |

FOREIGN PATENT DOCUMENTS

KR    1020060115610 A1    11/2006

OTHER PUBLICATIONS

Related International Patent Application No. PCT/US08/52058; Search Report dated Jun. 10, 2008, 3 pgs.

* cited by examiner

*Primary Examiner*—Allen C. Ho
(74) *Attorney, Agent, or Firm*—Fitch, Even, Tabin & Flannery

(57) ABSTRACT

One provides (101 and 102) two or more X-ray sources (202 and 204) that are independent and discrete from one another. By one approach, these X-ray sources emit corresponding X-rays (203 and 205) using different voltage levels. In particular, these voltage levels can be sufficiently different from one another to readily permit different elements as comprise an object (201) being examined to be distinguished from one another. These X-rays are then emitted (106) from these sources and towards an object to be examined while causing relative motion (207) between such sources on the one hand and the object on the other.

21 Claims, 2 Drawing Sheets

METHOD AND APPARATUS TO FACILITATE PROVISION AND USE OF MULTIPLE X-RAY SOURCES

TECHNICAL FIELD

This invention relates generally to object imaging and more particularly to X-ray-based object imaging.

BACKGROUND

The use of high energy rays, such as X-rays, to render images of visibly occluded objects is known in the art. This includes the non-film-based use of X-rays to non-destructively examine the contents of cargo containers or the like to facilitate an inspection for illegal and/or dangerous objects. An increased risk of terrorist activity has brought a corresponding increased interest in effectively and efficiently applying such technology to facilitate the detection of objects of particular concern such as conventional and/or nuclear explosive devices and payloads.

Notwithstanding such interest, present practices in this regard tend to often yield insufficient information with respect to permitting a relatively rapid conclusion to be drawn regarding a given object's standing as a benign item or a potential threat that merits further investigation. In particular, many such prior imaging practices yield information regarding a given object's shape but not necessarily a sufficient quantity of information regarding the object's chemical constituency. To put it more pointedly, and as a significant though not exclusive example, many such prior approaches are unable to provide relatively direct information regarding whether a given object is comprised of nuclear materials or something of less concern.

BRIEF DESCRIPTION OF THE DRAWINGS

The above needs are at least partially met through provision of the method and apparatus to facilitate provision and use of multiple x-ray sources described in the following detailed description, particularly when studied in conjunction with the drawings, wherein.

Figure 1:
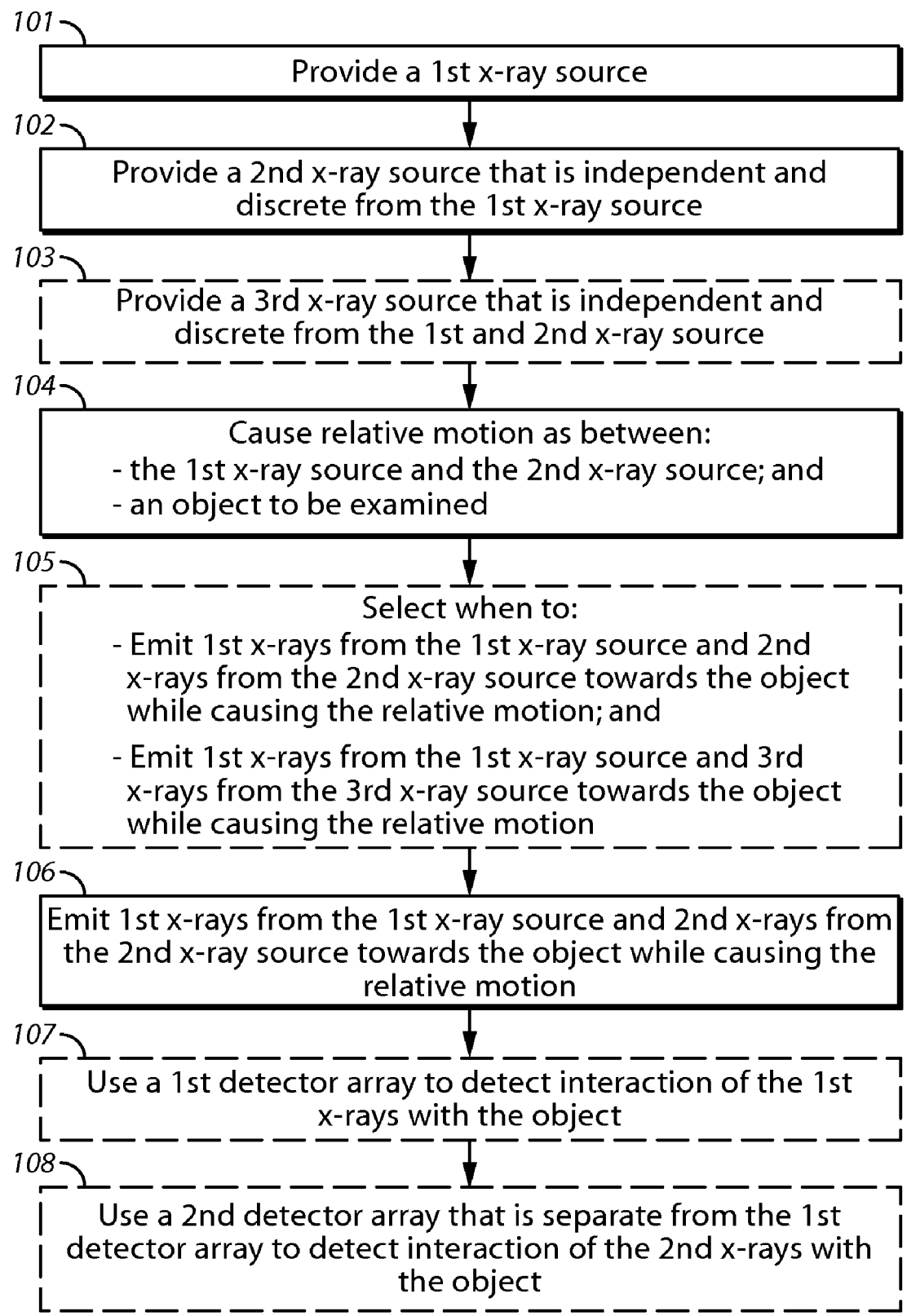
FIG. 1 comprises a flow diagram as configured in accordance with various embodiments of the invention.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. It will further be appreciated that certain actions and/or steps may be described or depicted in a particular order of occurrence while those skilled in the art will understand that such specificity with respect to sequence is not actually required. It will also be understood that the terms and expressions used herein have the ordinary meaning as is accorded to such terms and expressions with respect to their corresponding respective areas of inquiry and study except where specific meanings have otherwise been set forth herein.

DETAILED DESCRIPTION

Generally speaking, pursuant to these various embodiments, one provides two or more X-ray sources that are independent and discrete from one another. By one approach, these X-ray sources emit corresponding X-rays using different voltage levels. In particular, these voltage levels can be sufficiently different from one another to readily permit different elements as comprise an object being examined to be distinguished from one another. These X-rays are then emitted from these sources and towards an object to be examined while causing relative motion between such sources on the one hand and the object on the other.

By one approach, such relative motion comprises causing the object to move while the sources remain stationary. By another approach, such relative motion comprises causing the sources to move while the object remains stationary. By yet another approach, if desired, such relative motion can comprise moving both the object and one or more of the sources as well.

These teachings will also accommodate providing three or more X-ray sources as desired. In such a case, a determination can be made regarding which two sources of the three or more available sources to employ when examining a particular object. Such a selection might be based, for example, upon the overall weight of the object being examined (where, for example, greater weight tends to lead towards use of higher voltage X-ray sources).

So configured, the response of different elements with significantly different atomic numbers are different enough at the two X-ray energies being employed to enable such different elements to be distinguished from one another. In particular, the atomic number of the elements being examined can be readily estimated in this manner. Those skilled in the art will appreciate that such information can be gleaned via these teachings in a relatively quick and automated fashion. This, in turn, permits a relatively larger number of objects to be reliably examined in a considerably reduced amount of time as compared to prior practices in this regard. By one approach, for example, these teachings can be employed during a single pass of the object with respect to the multiple X-ray sources.

These teachings are therefore seen to provide considerably better information, in a same or reduced amount of time, as might ordinarily be expected when employing high energy examination sources. These teachings are particularly suitable for use in detecting nuclear materials that can comprise a key element in a fission, fusion, or so-called dirty bomb (where the nuclear materials are not intended to detonate per se but are to simply become dispersed as a consequence of a conventional explosion). These teachings are therefore seen to provide a significant tool in stemming the risks associated with terrorist ambitions.

Figure 2:
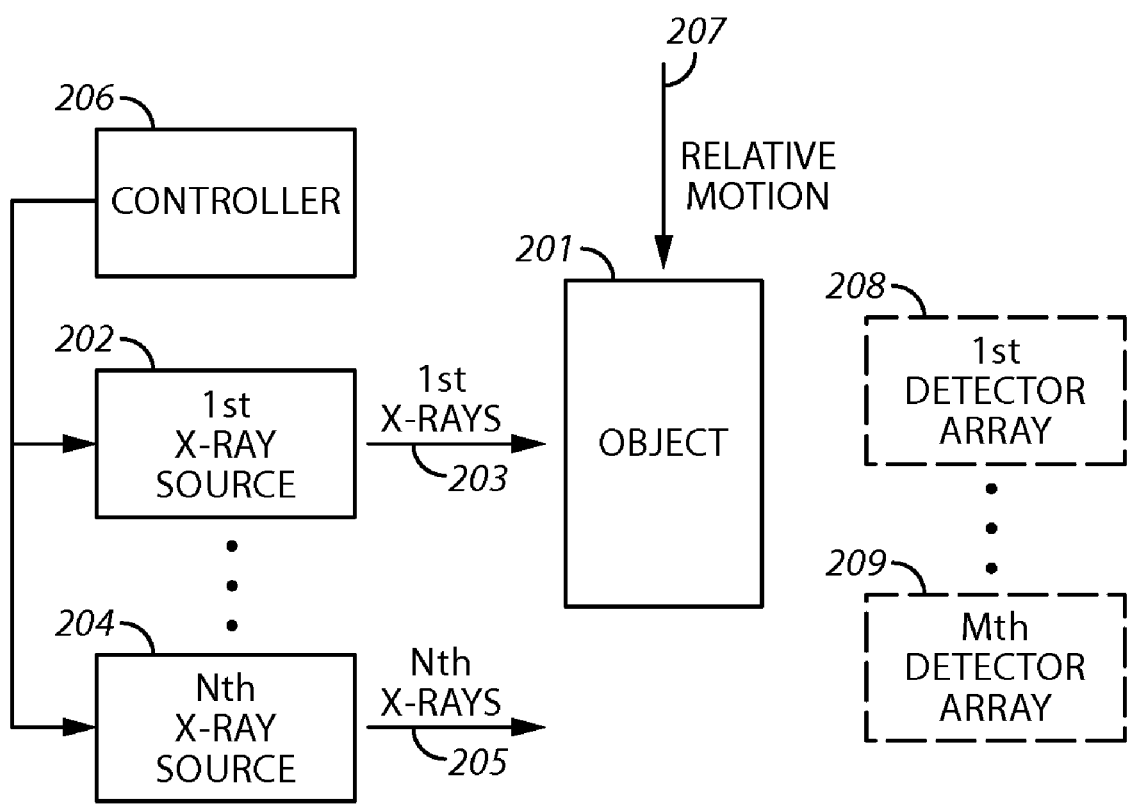
FIG. 2 comprises a block diagram as configured in accordance with various embodiments of the invention.

These and other benefits may become clearer upon making a thorough review and study of the following detailed description. Referring now to the drawings, and in particular to FIGS. 1 and 2, these teachings comprise a process 100 that facilitates the provision of a particular apparatus 200 and use of that apparatus 200 to examine a given object 201 (such as cargo, including but not limited to cargo contained within a cargo shipping container as is known in the art).

This process 100 provides for provision 101 of a first X-ray source 202 that is capable of selectively emitting first X-rays 203 and for provision 102 of a second X-ray source 204 that is capable of selectively emitting second X-rays 205. (FIG. 2 presents this second X-ray source 204 as an Nth X-ray source to illustrate that this process 100 will further optionally accommodate, if desired, providing 103 at least a third X-ray source. The possible use and benefits of such additional X-ray sources will be noted below where appropriate.) These various X-ray sources are independent and discrete from one another (though these teachings will readily accommodate, if desired, having one or more of these X-ray sources, such as the first X-ray source 202, comprise a selectable multi-voltage level X-ray source as is known in the art). As these various X-rays are shown as being at least substantially parallel to one another, the resultant corresponding image planes will similarly be substantially similar to one another.

By one approach, these various X-ray sources use different voltage levels. To illustrate, the first X-ray source 202 can emit first X-rays 203 using a first voltage level while the second X-ray source 204 emits second X-rays 205 using a second voltage level that is different from the first voltage level. This difference should be significant enough to readily permit different elements as comprise the object 201 to be distinguished from one another.

The amount of this difference can vary with the needs of a given expected application setting. In general, the amount of the difference can vary, at least in part, with respect to the degree by which various materials of interest (having different effective atomic numbers) have different coefficients for the three primary mechanisms of X-ray absorption (these being the photoelectric, Compton, and pair production mechanisms). In general, the further apart these atomic numbers are, the greater the difference between these coefficients.

By one approach, then, the first X-ray source 202 can comprise a 9 MV X-ray source while the second X-ray source 204 can comprise a 6 MV X-ray source. Other energy levels can of course be employed as desired and/or as may particularly suit the specific needs and/or opportunities of a given application setting.

Those skilled in the art will also understand and appreciate that the lower of the two (or more) energies should nevertheless be sufficient to penetrate the thickness and density of the target object. For example, while voltages of between 60 and 120 kV are sufficient to distinguish soft tissue from bone in the human body, voltages of between 120 and 180 kV may be necessary to distinguish conventional explosives from innocent materials in luggage and voltages of between 6 and 9 MV may be necessary to distinguish nuclear materials from ordinary metals in thick, high-density objects (with perhaps only 3 and 6 MV being necessary to distinguish such materials in objects that are easier to penetrate).

By one approach, these X-ray sources can be configured and arranged to provide X-rays that comprise X-ray fan beams. One or more collimators can be employed in known manners to achieve such a result. Such collimators, anti-scatter vanes, and/or other guards can also be employed to reduce or eliminate interference or other crosstalk between such X-rays if desired. By one approach, such techniques can serve to cause the X-rays as are emitted by the various X-ray sources to occur in different image planes. For example, the first X-rays can be emitted in a first image plane while the second X-rays are emitted in a second image plane that is different than the first image plane.

These teachings will also accommodate providing detector arrays to detect the aforementioned X-rays. By one approach, there can be a one-to-one correspondence between the number of detector arrays and the number of X-ray sources. In such a case, for example, one can provide a first detector array 208 through an Mth detector array 209 where M equals N (the number of X-ray sources as described above). These teachings will also accommodate, however, using a lesser number of detector arrays. For example, when N equals three (as when three X-ray sources are provided), M may equal two (thereby providing only two detector arrays). In such a case, and as will be shown below, the two available detector arrays are then used in conjunction with the two active X-ray sources. By way of illustration and not as a specific limitation with respect to these teachings, such detectors can be separated from their corresponding X-ray source by a distance of, for example, 39 feet.

Those skilled in the art will understand and realize that such detector arrays should typically be well aligned with their corresponding X-ray sources in order to provide best results. By one approach, such alignment can be attained and preserved by physically coupling each detector array/X-ray source pair such that these components, once calibrated with respect to their desired alignment, will not likely become readily misaligned during usage. By another approach, however, such components can be relatively movable with respect to one another (as may be appropriate, for example, when employing a greater number of X-ray sources than detector arrays). In such a case, graticule-controlled alignment mechanisms as are known in the art can be employed to facilitate dynamic configuration of each source/detector pair. Such alignment can be further augmented, if desired, by fine adjustments based, for example, upon a laser beam-based alignment process as is also known in the art.

This process 100 then provides for causing 104 relative motion 207 as between the first and second X-ray source 202 and 204 on the one hand and the object 201 to be examined on the other hand. The aforementioned controller 206 can be further configured to cause this relative motion, again in accordance with these teachings. As noted above, such relative motion 207 can comprise any of a variety of combinations of mobility and stationary presence amongst these various elements. The general purpose of such relative motion 207 is to tend to ensure that all portions of the object 201 are subjected to the first and second X-rays 203 and 205 as sourced by the aforementioned sources 202 and 204 as described below. The speed of such relative motion 207 can vary with the needs and/or opportunities as tend to characterize a given application setting.

As noted above, this process 100 can accommodate providing more than two such X-ray sources. In such a case, this process 100 will also further accommodate selecting a particular pair of X-ray sources to use with respect to a given object 201. To illustrate, and referring still to FIG. 1, when three such X-ray sources are provided this process 100 can optionally provide for selecting 105 when to emit first X-rays from the first X-ray source and second X-rays from the second X-ray source towards the object 201 while causing the relative motion 207 and when to emit first X-rays from the first X-ray source and third X-rays from the third X-ray source towards the object 201 while causing the relative motion 207.

Such a selection can be based upon such criteria as may be viewed as important in a given application setting. As one illustrative example in this regard, such a selection could be based upon some general characterization of choice of the object 201 (such as, but not limited to, the object's thickness and/or weight). For example, two relatively lower-energy X-ray sources may be so selected 105 when the weight of the object 201 is relatively lower and two relatively higher-energy X-ray sources may be so selected 105 when the weight of the object 201 is relatively higher. Other possibilities exist as well as will be understood by those skilled in the art.

In any event, this process 100 then provides for emitting 106 X-rays from the available and/or selected X-ray sources while causing the aforementioned relative motion 207. When the provided X-ray sources comprise the aforementioned first and second X-ray sources, this can comprise emitting first X-rays from the first X-ray source and second X-rays from the second X-ray source. By one approach, if desired, both X-ray sources can emit their corresponding X-rays in a temporally simultaneous or otherwise at least partially overlapping manner. By another approach, however, these X-ray sources can emit their corresponding X-rays in an alternating manner to avoid, fully or at least partially, any temporal overlap with respect to their presence. As noted above, these emissions can continue for a sufficient duration of time to ensure that all (or at least a desired portion) of the object 201 is suitably exposed to such energy.

This process 100 will then accommodate using 107 a first detector array 208 to detect interaction of the first X-rays 203 with the object 201 and using 108 a second detector array 209 to detect interaction of the second X-rays 205 with the object 201. The use of detector arrays in such a manner, and the proper processing of the received information to develop image information corresponding to an illuminated object comprises a well-understood area of endeavor. As the present teachings are not particularly sensitive to the selection of any particular approach in this regard, for the sake of brevity and the preservation of narrative focus further elaboration regarding such processing is not provided here.

It will be understood by those skilled in the art, however, that such information, which corresponds to image information developed by the use of two considerably different energy levels, can be readily employed to ascertain the relative atomic number(s) as pertain to the constituent elements of the object being examined. This will typically comprise registering the two resultant image planes with one another to facilitate analyzing the entire cargo contents for corresponding information regarding the estimated atomic number composition. Those skilled in the art will know that there are various ways by which such registration can be achieved for such purposes, including use of a mechanical calibration component and/or an image registration algorithm software component.

This, in turn, permits ready determination regarding when a given object comprises, in whole or in part, elements of concern such as any of a plurality of forms of plutonium, uranium, or the like. Those skilled in the art will further recognize and appreciate that these teachings are readily employed in conjunction with existing technology and can greatly facilitate the efficient, reliable, and relatively rapid detection of elements of concern in addition to other characterizing attributes that are otherwise ordinarily available through X-ray-based inspection systems.

Those skilled in the art will also appreciate and understand that the aforementioned use of two separate X-ray sources (as versus a single source capable of emitting variable levels of energy) produces more photons per detector than can be achieved with a single source and hence yields less noise and overall better imaging performance. This configuration also permits beam filters for each X-ray source to be optimized for a given energy level rather than requiring the use of a compromise filter that must serve the potential application of a wide range of energy levels.

This dual source approach also permits the corresponding detector arrays to be more precisely suited to a given source having a given energy level. For example, larger detectors can be used with the lower energy X-ray source (which will tend to serve mainly to provide input to facilitate the above-described materials discrimination capability) while smaller detectors can be used with the higher energy X-ray source without compromising such discrimination capability.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept. For example, the present teachings are readily employed in conjunction with any of a variety of known (or hereafter developed) display, alarm, and/or other user interface components and techniques. As another example, these teachings can be employed in conjunction with multiple passes where, for example, a second pass involves use of one or more different voltages and/or different speeds of relative movement in order to obtain more, or different, kinds of information as may have been obtained during a first pass.

I claim:

1. A method comprising:
   providing a first X-ray source;
   providing at least a second X-ray source that is independent and discrete from the first X-ray source;
   providing at least a third X-ray source that is independent and discrete from the first X-ray source and the second X-ray source;
   selecting when to:
      emit X-rays from the first X-ray source and X-rays from the second X-ray source towards an object while causing relative motion between the object and the X-ray sources; and
      emit X-rays from the first X-ray source and X-rays from the third X-ray source towards the object while causing relative motion between the object and the X-ray sources;
   to thereby provide a selected first X-ray source and an additional X-ray source and an unselected X-ray source;
   causing relative motion as between:
      (1) the selected first X-ray source and the additional X-ray source; and
      (2) an object to be examined;
   emitting first X-rays from the first X-ray source and second X-rays from the additional X-ray source, but not emitting X-rays from the unselected X-ray source, towards the object while causing the relative motion to thereby provide substantially similar image planes as correspond to the object.

2. The method of claim 1 wherein the object comprises cargo.

3. The method of claim 2 wherein the object comprises cargo contained within a cargo shipping container.

4. The method of claim 1 wherein causing relative motion comprises at least one of:
   causing the first X-ray source and the additional X-ray source to move;
   causing the object to move.

5. The method of claim 1 wherein causing relative motion comprises causing the relative motion in a single pass.

6. The method of claim 1 wherein emitting first X-rays from the first X-ray source and second X-rays from the additional X-ray source comprises emitting a first X-ray fan beam from the first X-ray source and a second X-ray fan beam from the additional X-ray source.

7. The method of claim 1 further comprising:
   using a first detector array to detect interaction of the first X-rays with the object;

using a second detector array that is separate from the first detector array to detect interaction of the second X-rays with the object.

8. The method of claim 1 wherein emitting first X-rays from the first X-ray source and second X-rays from the additional X-ray source towards the object while causing the relative motion further comprises alternating emitting the first X-rays with emitting the second X-rays.

9. The method of claim 1 wherein selecting comprises selecting as a function, at least in part, of a general characterization of the object.

10. The method of claim 1 wherein the first X-ray source comprises a selectable multi-voltage level X-ray source.

11. An apparatus comprising:
a first X-ray source;
at least a second X-ray source that is independent and discrete from the first X-ray source;
at least a third X-ray source that is independent and discrete from the first X-ray source and the second X-ray source;
a controller configured and arranged to:
select when to:
emit X-rays from the first X-ray source and X-rays from the second X-ray source towards an object while causing relative motion between the object and the first and second X-ray source; and
emit X-rays from the first X-ray source and X-rays from the third X-ray source towards the object while causing relative motion between the object and the first and third X-ray source;
to thereby provide a selected first X-ray source and an additional X-ray source and an unselected X-ray source;
cause relative motion as between:
(1) the selected first X-ray source and the additional X-ray source; and
(2) an object to be examined; and to
emit first X-rays from the first X-ray source and second X-rays from the selected X-ray source, but not emit X-rays from the unselected X-ray source, towards the object while causing the relative motion to thereby provide substantially similar image planes as correspond to the object.

12. The apparatus of claim 11 wherein:
the first X-ray source emits the first X-rays using a first voltage level;
the additional X-ray source emits the second X-rays using a second voltage level that is different from the first voltage level.

13. The apparatus of claim 12 wherein the second voltage level is sufficiently different from the first voltage level to readily permit different elements as comprise the object to be distinguished from one another.

14. The apparatus of claim 11 wherein the object comprises cargo.

15. The apparatus of claim 14 wherein the object comprises cargo contained within a cargo shipping container.

16. The apparatus of claim 11 wherein the controller is configured and arranged to cause the relative motion by at least one of:
causing the selected first X-ray source and the additional X-ray source to move;
causing the object to move.

17. The apparatus of claim 11 wherein the controller is configured and arranged to cause the relative motion in a single pass.

18. The apparatus of claim 11 wherein the first X-rays from the first X-ray source comprise an X-ray fan beam and the second X-rays from the selected X-ray source comprise a second X-ray fan beam.

19. The apparatus of claim 11 further comprising:
a first detector array configured and arranged to detect interaction of the first X-rays with the object;
a second detector array that is separate from the first detector array and that is configured and arranged to detect interaction of the second X-rays with the object.

20. The apparatus of claim 11 wherein the controller is further configured and arranged to alternate emitting the first X-rays with emitting the second X-rays while causing the relative movement.

21. The apparatus of claim 11 wherein the first X-ray source comprises a selectable multi-voltage level X-ray source.

* * * * *